United States Patent [19]
Bird et al.

[11] Patent Number: 5,569,829
[45] Date of Patent: Oct. 29, 1996

[54] TRANSFORMED TOMATO PLANTS

[75] Inventors: Colin R. Bird, Bracknell; Jeremy M. Boniwell, Marston; Donald Grierson, Shepshed; John A. Ray, Wooden Hill; Wolfgang W. Schuch, Crowthorne, all of United Kingdom

[73] Assignee: Imperial Chemical Industries, London, England

[21] Appl. No.: 73,425

[22] Filed: Jun. 9, 1993

Related U.S. Application Data

[63] Continuation-in-part of Ser. No. 598,873, filed as PCT/GB93/00021 Jan. 8, 1993, Pat. No. 5,254,800.

[30] Foreign Application Priority Data

Oct. 20, 1989 [GB] United Kingdom .................. 8923716
Jan. 10, 1992 [GB] United Kingdom .................. 9200520

[51] Int. Cl.⁶ ........................................................ A01H 4/00
[52] U.S. Cl. ................ 800/205; 435/172.3; 800/DIG. 44
[58] Field of Search ........................... 435/172.3, 240.4, 435/320.1; 800/200, 205, DIG. 44

[56] References Cited

U.S. PATENT DOCUMENTS

| | | | |
|---|---|---|---|
| 4,801,540 | 1/1989 | Hiatt et al. | 435/240.4 |
| 5,107,065 | 4/1992 | Shewmaker et al. | 800/205 |

FOREIGN PATENT DOCUMENTS

WO9105865  5/1991  WIPO.

OTHER PUBLICATIONS

Maunders et al, "Ethylene stimulates the accumulation for ripening–related mRNAs in tomatoes", Plant, Cell and Environment (1987) 10, 177–184.

Slater et al, "Isolation and characterisation of cDNA clones for tomato polygalacturonase and other ripening–related proteins", Plant Molecular Biology (1985) 5, 137–147.

Smith et al, "Antisense RNA inhibition of polygalactyuronase gene expression in transgenic tomatoes", Nature (1988) 334, 724–726.

Grierson et al, Phil. Trans., R. Soc. Lond. B314, 399–410 (1986).

Schuch et al, Plant Molecular Biology (1989) 13, 303–311.

Tanksley, et al (1988) Theor Appl Genet. 75:811–823.

Tieman et al (Jun. 1992) The Plant Cell 4:667–679.

Boswell, et al in *Computational Molecular Biology* (Tesk, ed) Oxford University Press, Oxford, 1988, pp. 170–171.

*Primary Examiner*—Che S. Chereskin
*Attorney, Agent, or Firm*—Cushman Darby & Cushman

[57] ABSTRACT

A method is provided for making fruit (particularly tomatoes) having increased solids content which comprises cultivating fruit-bearing plants in which expression of genes homologous to pTOM36 is at least partially inhibited. For this purpose the fruit may be transformed with DNA constructs comprising a DNA sequence homologous to some or all of the gene encoded by the clone pTOM36. The clone is adapted to generate sense or antisense RNA under control of a plant promoter.

2 Claims, 5 Drawing Sheets

FIG. 1A

```
         10         20         30         40         50         60         70
ATGGTAAATT GCAATGGTGA AGGAGTCTTG TTTATCGAAG GTGATGCTAA TATAGAGCTT GAAAAATTAG 80         90        100        110        120        130        140
GTGAATCTAT TAAGCCACCA TGTCATACTT GGATTTACTA CTTCATAAATG TTCATGGTTC TGATGGAATT 150        160        170        180        190        200        210
ATTGGTTCTC CTCTTTTGTT AATTCAGGTG ACTCGTTTTA CTTGTGGTGG ATTTGCTGTT GGATTTAGAT 220        230        240        250        260        270        280
TTAATCACAC AATGATGGAT GCTTATGGCT TCAAAAATGTT TCTAAATGCG TTAAGTGAAT TAATTCAAGG 290        300        310        320        330        340        350
AGCTTCAACA CCTTCTATAT TGCCTGTATG GGAAAGACAT CTCCTAAGTG CTAGATCATC ACCAAGTATT
```

FIG. IB

```
       360        370        380        390        400        410        420
ACATGTATTC ATCATGAGTT TGATGAGGAA ATTGAATCAA AAATTGCGTG GGAATCTATG GAAGATAAGT 430        440        450        460        470        480        490
TGATACAACA ATCATTTTTC TTTGGAAATG AGGAGATGGA AGTCATTAAA AATCAAGTTC CTCCAAATTA 500        510        520        530        540        550        560
TGAATGTACA AAATTCGAGT TATTAATGGC ATTTTTATGG AAAATGTCGTA CCATTGCTCT TAATTTGCAC 570        580        590        600        610        620        630
TCTGATGAAA TTGTTCGTTT GACATACGTT ATTAATATAC GTGGAAAAAA GTCACTCAAC ATTGAATTAC 640        650        660        670        680        690        700
CAATTGGTTA TTATGGGAAT GCGTTTATTA CTCCAGTTGT TGTATCAAAA GCAGGTTTGT TATGTTCAAA
```

FIG. IC

```
         710        720        730        740        750        760        770
TCCAGTGACA TATGCAGTTG AATTGATCAA GAAAGTTAAA GATCATATAA ATGAAGAATA CATCAAATCA 780        790        800        810        820        830        840
TTGATAGATT TAATGGTTAC TAAAGGGAGA CCAGAGTTAA CAAATCTTGG AATTTTTTGG TCTCAGATAA 850        860        870        880        890        900        910
TAGAATATATT GGATTTGATG AATTTGATTT TGGATGGGGA AACCCCATTT TTGGAGGGAT CTTAAAGGCT 920        930        940        950        960        970        980
ATATCTTTCA CTAGTTTTGG TGTTTCTGTT AAAAATGACA AAGGAGAAAA AGGTGTTTTG ATAGCTATAA 990       1000       1010       1020       1030       1040       1050
GTTTACCTCC ATTGGCCATG AAAAAAACTTC AAGATATCTA CAACATGACT TTCAGAGTCA TAATTTCAAA 1060       1070       1080
TATATAGGCT TTTCTATTGA AAAAAAAAAA
```

| Oligo | 5' | | 3' |
|---|---|---|---|
| T36AS-1 | GGGGGGGATCCTAAAATTGCAATGGTGAAGGAGTCTTG (xx above BamHI site) | | |
| T36AS-2 | (xxxxx) GGTACCAATAGAAAAGCCTATATATTTGAAATTATGACTCTGAAAG (KpnI) | | |
| T36AS-3 | (xxxxx) GGTACCGACATTTCCATAAAAAATGCCATTAATAACTCGAATTTTGTACATTC (KpnI) | | |
| T36AS-4 | CCAATAATTCCATCGG(xx)TACCATGAACATTATGAAGTAGTAAATCCAAG (KpnI) | | | x = base change or addition

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 1080 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( v i ) ORIGINAL SOURCE:
    ( A ) ORGANISM: Lycopersicon esculentum
    ( B ) STRAIN: Ailsa Craig
    ( D ) DEVELOPMENTAL STAGE: Ripening ( x i ) SEQUENCE DESCRIPTION: SEQ ID NO:1:

```
ATGGTAAATT GCAATGGTGA AGGAGTCTTG TTTATCGAAG GTGATGCTAA TATAGAGCTT      60
GAAAAATTAG GTGAATCTAT TAAGCCACCA TGTCATACTT GGATTTACTA CTTCATAATG     120
TTCATGGTTC TGATGGAATT ATTGGTTCTC CTCTTTTGTT AATTCAGGTG ACTCGTTTTA     180
CTTGTGGTGG ATTTGCTGTT GGATTTAGAT TTAATCACAC AATGATGGAT GCTTATGGCT     240
TCAAAATGTT TCTAAATGCG TTAAGTGAAT TAATTCAAGG AGCTTCAACA CCTTCTATAT     300
TGCCTGTATG GGAAAGACAT CTCCTAAGTG CTAGATCATC ACCAAGTATT ACATGTATTC     360
ATCATGAGTT TGATGAGGAA ATTGAATCAA AAATTGCGTG GAATCTATG GAAGATAAGT      420
TGATACAACA ATCATTTTTC TTTGGAAATG AGGAGATGGA AGTCATTAAA AATCAAGTTC     480
CTCCAAATTA TGAATGTACA AAATTCGAGT TATTAATGGC ATTTTTATGG AAATGTCGTA     540
CCATTGCTCT TAATTTGCAC TCTGATGAAA TTGTTCGTTT GACATACGTT ATTAATATAC     600
GTGGAAAAAA GTCACTCAAC ATTGAATTAC CAATTGGTTA TTATGGGAAT GCGTTTATTA     660
CTCCAGTTGT TGTATCAAAA GCAGGTTTGT TATGTTCAAA TCCAGTGACA TATGCAGTTG     720
AATTGATCAA GAAAGTTAAA GATCATATAA ATGAAGAATA CATCAAATCA TTGATAGATT     780
TAATGGTTAC TAAAGGGAGA CCAGAGTTAA CAAATCTTGG AATTTTTTGG TCTCAGATAA     840
TAGATATATT GGATTTGATG AATTTGATTT TGGATGGGGA AACCCCATTT TTGGAGGGAT     900
CTTAAAGGCT ATATCTTTCA CTAGTTTTGG TGTTTCTGTT AAAAATGACA AAGGAGAAAA     960
AGGTGTTTTG ATAGCTATAA GTTACCTCC ATTGGCCATG AAAAAACTTC AAGATATCTA      1020
CAACATGACT TTCAGAGTCA TAATTTCAAA TATATAGGCT TTTCTATTGA AAAAAAAAAA    1080
```

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

```
GGGGGGGATC CTAAATTGCA ATGGTGAAGG AGTCTTG                               37
```

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

```
GGTACCAATA GAAAAGCCTA TATATTTGAA ATTATGACTC TGAAAG                     46
```

( 2 ) INFORMATION FOR SEQ ID NO:4:

( i ) SEQUENCE CHARACTERISTICS:
        ( A ) LENGTH: 52 base pairs
        ( B ) TYPE: nucleic acid
        ( C ) STRANDEDNESS: single (D) TOPOLOGY: linear (x i) SEQUENCE DESCRIPTION: SEQ ID NO:4:

GGTACCGACA TTTCCATAAA AATGCCATTA ATAACTCGAA TTTTGTACAT TC  52

(2) INFORMATION FOR SEQ ID NO:5:

(i) SEQUENCE CHARACTERISTICS:
      (A) LENGTH: 48 base pairs
      (B) TYPE: nucleic acid
      (C) STRANDEDNESS: single
      (D) TOPOLOGY: linear    (x i) SEQUENCE DESCRIPTION: SEQ ID NO:5:

CCAATAATTC CATCGGTACC ATGAACATTA TGAAGTAGTA AATCCAAG  48

TRANSFORMED TOMATO PLANTS

This is a continuation-in-part of Ser. No. 07/598,873, filed Oct. 19, 1990, now U.S. Pat. No. 5,254,800, and International Application No. GB93/00021, filed Jan. 8, 1993 designating the U.S. and claiming priority from U.K. Application No. 9200520.6, filed Jan. 10, 1992.

This application relates to novel DNA constructs, plant cells containing them and plants derived therefrom. It involves the use of sense or antisease RNA technology to control gene expression in plants.

As is well known, a cell manufactures protein by transcribing the DNA of the gene for that protein to produce messenger RNA (mRNA), which is then processed (eg by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, for example in European Patent publication no 271988 to ICI (corresponding to U.S. Ser. No. 119614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the amount of polygalacturonase and reduction in depolymerisation of pectins during tomato fruit ripening (Smith et al, Nature, 334, 724–726, 1988; Smith et al., manuscript submitted for publication). Thus antisense RNA has been proven to be useful in achieving downregulation of gene expression in plants.

In work leading to the present invention we have identified a gene which expresses an enzyme involved in the ripening of tomatoes. This gene has been cloned and characterised. We propose that inhibition of this gene be used to produce tomatoes and other fruit having an increased solids content. The gene in question is encoded (almost completely) in the clone pTOM36.

In particular, we have identified in tomato fruit downregulated for production of the gene pTOM36 the properties of increased solids content; and of higher content of reducing sugars, for example glucose and fructose.

Accordingly, according to the present invention we provide a method of producing fruit, especially tomato fruit, having an increased solids content, which comprises cultivating plants in which expression of genes homologous to pTOM36 is at least partially inhibited. Such inhibition may conveniently be achieved by transforming plants with suitable constructs containing the gene pTOM36, or part thereof. Fruit according to this aspect of the invention are particularly useful for making processed food products, for example tomato paste or tomato soup.

Increased fruit solids has been a major target of breeding for processing cultivars of several crops for many years. Improved flavour is also a breeding target for all fruit crops, especially in cultivars for the fresh market.

The quality of paste produced from processed tomatoes is in part related to the viscosity of the product which is usually determined by the Bostwick flow rate, reduced flow rate being desirable. The factors that interact to give a thicker product with reduced flow rate are complex, involving interactions between insoluble and soluble components. The characteristics of components in whole fruit will change during processing because of enzyme action and chemical changes brought about by heating which is involved in tomato processing by the so-called "hot-break" method.

The consistency of hot break paste is improved by increasing the level of solids in the whole fruit used in processing. Increased levels of soluble and insoluble solids in processing tomatoes has been an object of plant breeders for many years.

Soluble solids are the solutes in the tomato serum and consists primarily of carbohydrates. In ripe fruit, hexoses are the primary component of the soluble solids and account for about 50% of the fruit dry weight. The free sugars are mainly glucose and fructose; sucrose is present but rarely exceeds 1% of the dry weight. Paste is normally sold on the basis of its natural tomato soluble solids (NTSS) content. Because the sugars are the major contributors to NTSS, a higher sugar content contributes to a higher yield of paste per tonne of tomatoes. The correlation between NTSS and total solids (TS) is very high, although the relationship varies amongst tomato cultivars. Sugar content is also a critical component of the flavour of tomatoes.

Insoluble solids (IS) consist mainly of the polysaccharides in the cell wall. Residual starch will also contribute to the IS although, in normal ripening, this forms a small component. The IS/TS ratio partially determines the consistency of tomato products. Where high consistency is required, a greater quantity of IS improves the product quality. IS are measured as both water-insoluble solids (WIS) and alcohol-insoluble solids (AIS). The AIS quantities are greater than those for WIS because smaller polysaccharides are less soluble in 80% ethanol than in water.

Thus, increasing the solids content is advantageous as it may improve the processing properties and/or texture and/or sweetness and/or taste of the fruit. Such an increase may be brought about by expression of a pTOM36 sense or antisense construct in fruits such as tomato, melon, peach, pear, etc.

DNA constructs useful in the invention comprise at least part of a DNA sequence homologous to pTOM36 adapted for expression under the control of a promoter functional in plants. The DNA sequence homologous to pTOM36 may be arranged to express mRNA that is homologous with or complementary to (sense or antisense) natural pTOM36 mRNA. It preferably comprises a homologous base sequence at least 50 bases in length. There is no theoretical upper limit to the base sequence—it may be as long as the relevant mRNA produced by the cell—but for convenience it will generally be found suitable to use sequences between 100 and 1000 bases in length. Moreover, if the DNA is arranged to express sense RNA, the sequence is preferably shorter than full-length (i.e., long enough to code for a functional protein). Full-length sense sequences may (but do not necessarily) result in over-expression rather than inhibition.

The preferred source of DNA for use in the present invention is DNA derived from the clone pTOM36. The required DNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences. If antisense vectors are required, the cloning is carried out so that the DNA sequence is inverted with respect to its orientation in the strand from which it was cut. In the new vector, the strand that was formerly the template strand then becomes the coding strand, and vice versa. The new vector will thus encode RNA in a base sequence which is complementary to the sequence of pTOM36 mRNA. Thus the two RNA strands are complementary not only in their base sequence but also in their orientations (5' to 3').

As source of the DNA base sequence for transcription, it is convenient to use a cDNA clone such as pTOM36. The base sequence of pTOM36 is set out in FIGS. 1A–1C. Searches in DNA and protein data bases have not revealed any homology to known genes or proteins. This clone has been deposited at the National Collections of Industrial and Marine Bacteria, PO Box 31, of 23 St. Machar Drive (formerly of 135 Abbey Road), Aberdeen AB2 1RY, Scotland, as a plasmid in E.coli, under the reference NCIMB 40192, on 1 Sep. 1989. Alternatively, a cDNA clone similar to pTOM36 may be obtained from the mRNA of ripening tomatoes by the method described by Slater et al, Plant Molecular Biology 5, 137–147, 1985. In this way may be obtained sequences coding for the whole, or substantially the whole, of the mRNA produced by pTOM36. Suitable lengths of the cDNA so obtained may be cut out for use by means of restriction enzymes.

An alternative source of DNA for the base sequence for transcription is a suitable gene encoding a protein involved in fruit ripening. Such a gene may differ from the cDNA of pTOM36 in that introns may be present. The introns are not transcribed into mRNA (or, if so transcribed, are subsequently cut out). When using such a gene as the source of the base sequence for transcription it is possible to use either intron or exon regions.

A further way of obtaining a suitable DNA base sequence for transcription is to synthesis it ab initio from the appropriate bases, for example using FIG. 1 as a guide.

Recombinant DNA and vectors according to the present invention may be made as follows. A suitable vector containing the desired base sequence for transcription (for example pTOM36) is treated with restriction enzymes to cut the sequence out. The DNA strand so obtained is cloned (if desired in reverse orientation) into a second vector containing the desired promoter sequence (for example cauliflower mosaic virus 35S RNA promoter or the tomato polygalacturonase gene promoter sequence—Bird et al., Plant Molecular Biology, 11, 651–662, 1988) and the desired terminator sequence (for example the 3' of the Agrobacterium tumefaciens nopaline synthase gene, the nos 3' end).

According to the invention we propose to use both constitutive promoters (such as cauliflower mosaic virus 35S RNA) and inducible or developmentally regulated promoters (such as the ripe-fruit-specific polygalacturonase promoter) as circumstances require. Use of a constitutive promoter will tend to affect functions in all parts of the plant: while by using a tissue specific promoter, functions may be controlled more selectively. Thus in applying the invention, e.g. to tomatoes, it may be found convenient to use the promoter of the PG gene (Bird et al, 1988, cited above). Use of this promoter, at least in tomatoes, has the advantage that the production of RNA is under the control of a ripening-specific promoter. Thus the RNA is only produced in the organ in which its action is required. Other ripening-specific promoters that could be used include the E8 promoter (Diekman & Fischer, EMBO Journal 7, 3315–3320, 1988) and the promoters from the pTOM36 genes.

Vectors according to the invention may be used to transform plants as desired, to make plants according to the invention. Dicotyledonous plants, such as tomato, may be transformed by Agrobacterium Ti plasmid technology, for example as described by Bevan (1984) Nucleic Acid Research, 12, 8711–8721. Such transformed plants may be reproduced sexually, or by cell or tissue culture.

The degree of production of RNA in the plant cells can be controlled by suitable choice of promoter sequences, or by selecting the number of copies, or the site of integration, of the DNA sequences according to the invention that are introduced into the plant genome. In this way it may be possible to modify solids content to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, as well as tomatoes, fruits of such as mangoes, peaches, apples, pears, strawberries, bananas and melons.

As previously stated, the preferred source of antisense RNA for use in the present invention is DNA showing homology to the gene encoded by the clone pTOM36. pTOM36 was derived from a cDNA library isolated from ripe tomato RNA (Slater et al Plant Molecular Biology 5, 137–147, 1985). Four other clones (pTOM22, pTOM76, pTOM77, pTOM89) from the same library cross-hybridise to pTOM36 and probably contain related sequences. pTOM36 has been characterised by hybrid select translation, but there is some ambiguity about the results of these experiments. Slater et al (Plant Molecular Biology 5, 137–147, 1985) reported a product of 44 kD, whereas (Maunders et al Plant, Cell and Environment 10, 177–184, 1987) found that it encodes a protein of approximately 52,000 daltons. DNA sequence analysis has demonstrated that the clone is 1069 bases long with an open reading frame of 271 codons. It is believed to encode a cytoplasmic protein, as no apparent leader sequence was detected using computer analysis of the amino acid sequence derived from the DNA sequence.

We have shown that the mRNA for which pTOM36 codes is expressed in ripening tomato fruit. No expression could be detected in green fruit. pTOM36 is expressed most strongly at the full orange stage of ripening. The level of mRNA then declines in line with the general decline in synthetic capacity of the ripening fruit. Expression of pTOM36 mRNA could also be induced by exposing mature green fruit to exogenous ethylene. The expression of pTOM36 is reduced in the ripening inhibitor (rin) tomato fruit ripening mutant which mature very slowly. pTOM36 related sequences are also expressed in senescing leaves.

The genomic locations of sequences homologous to pTOM36 have been identified using RFLP mapping: three loci in the tomato genome carry sequences homologous to pTOM36. It has also been shown by Southern blotting that the gene may be present as a small multigene family. The individual members of the multigene family may be expressed differentially in ripening fruit and during senescence.

The invention will now be described further with reference to the accompanying drawings, in which.

The following Examples illustrate aspects of the invention.

EXAMPLE 1

Identification of base sequence of pTOM36

Figure 1A:
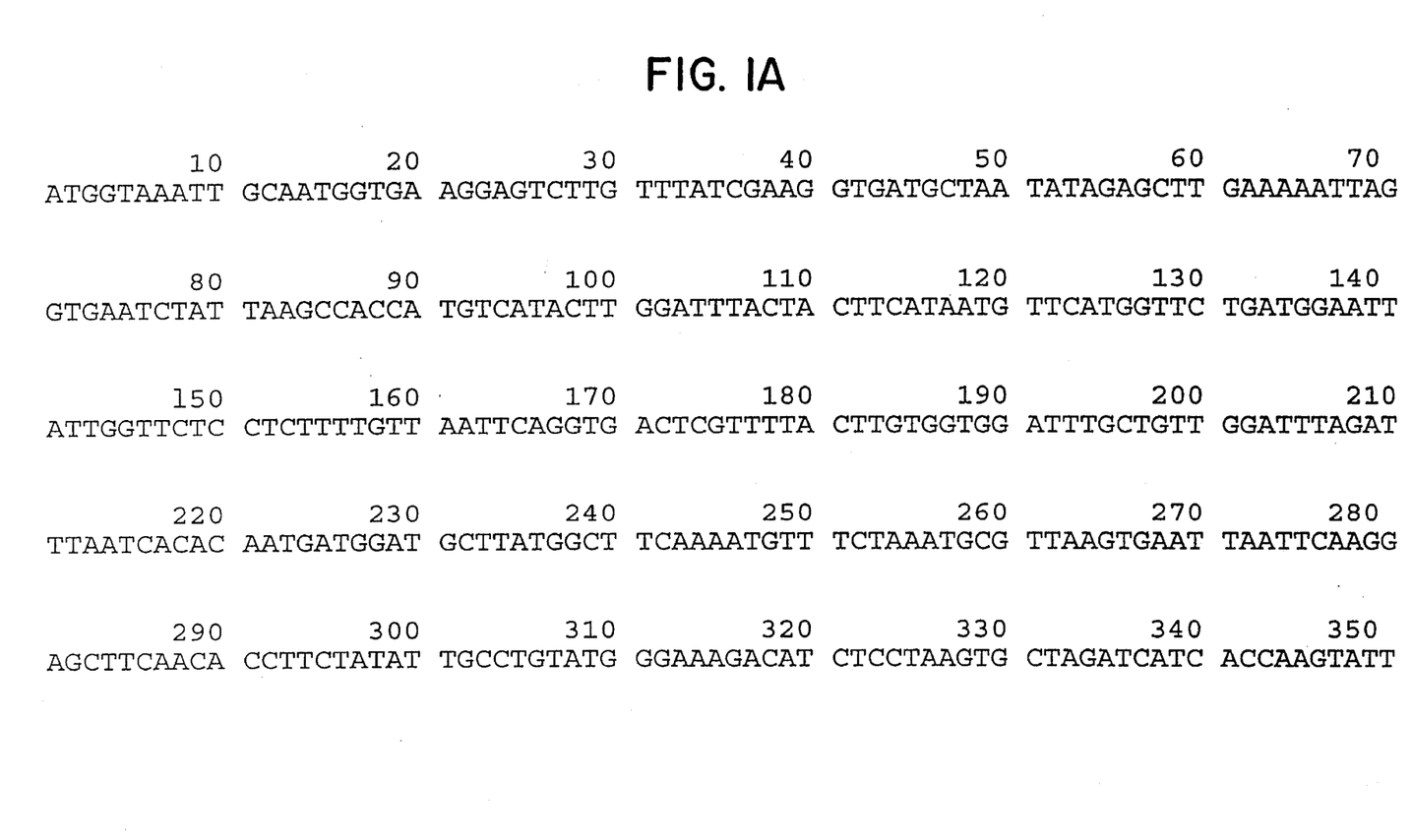
FIGS. 1A–1C show the base sequence of the clone pTOM36 (SEQ ID No:1)
Figure 1B:
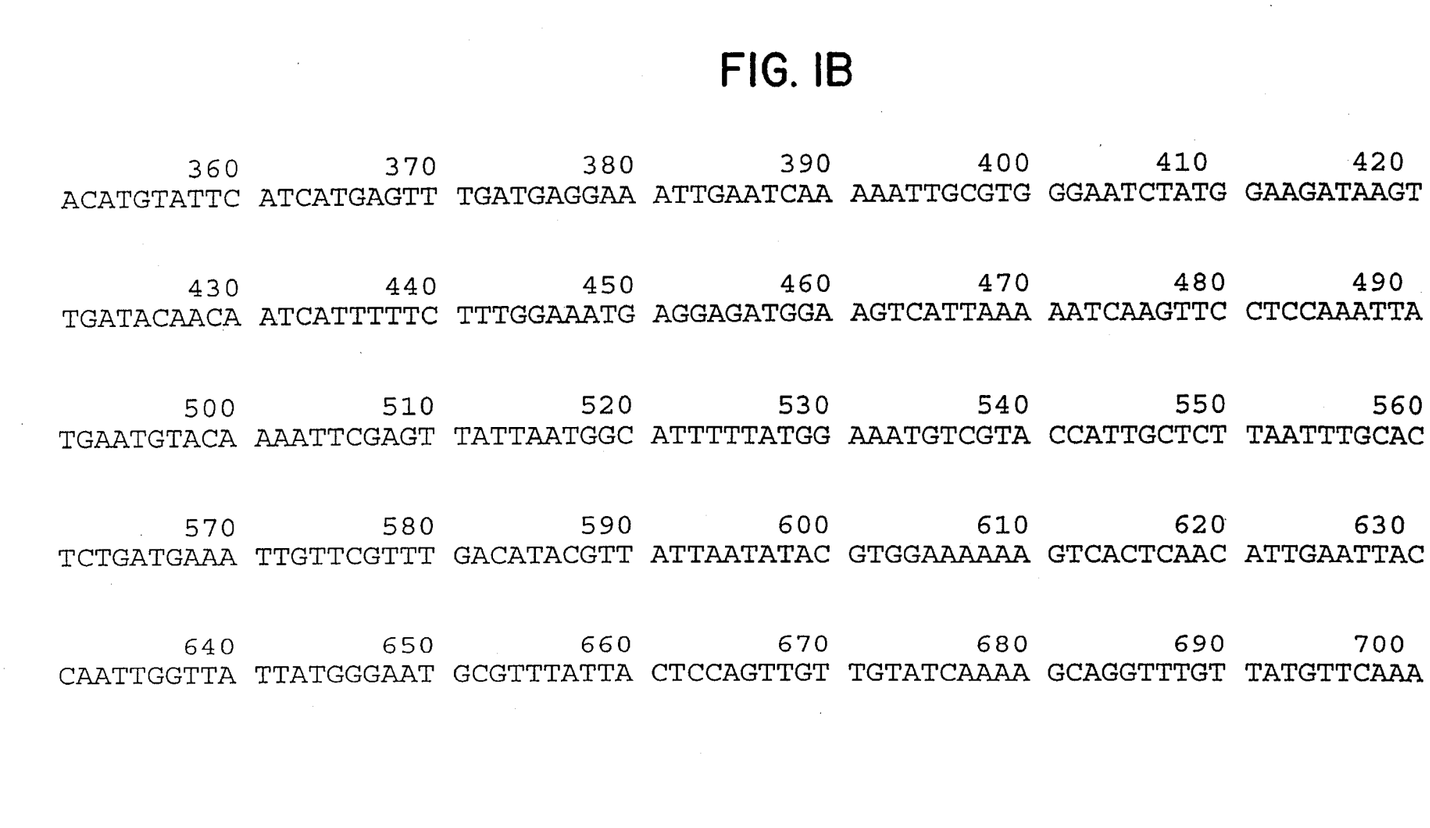
Figure 1C:
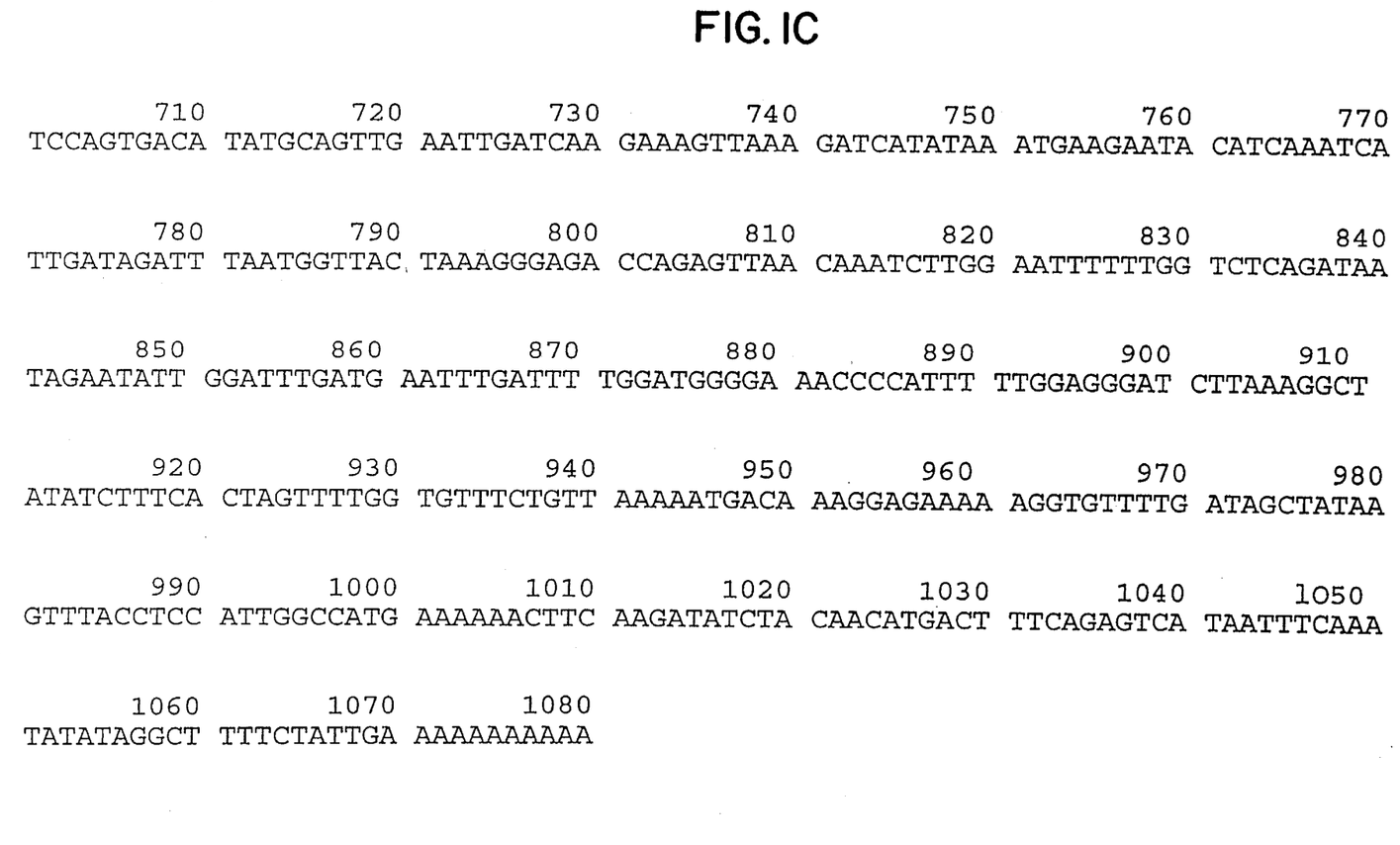

The base sequence of pTOM36 was determined by standard DNA sequencing procedures and is shown in FIGS. 1A–1C. Knowledge of this sequence is essential for determining the orientation of the open reading frame and for the subsequent construction of RNA antisense vectors.

EXAMPLE 2A

Construction of pTOM36 antisense RNA vectors with the CaMV 35S promoter

Figure 2:
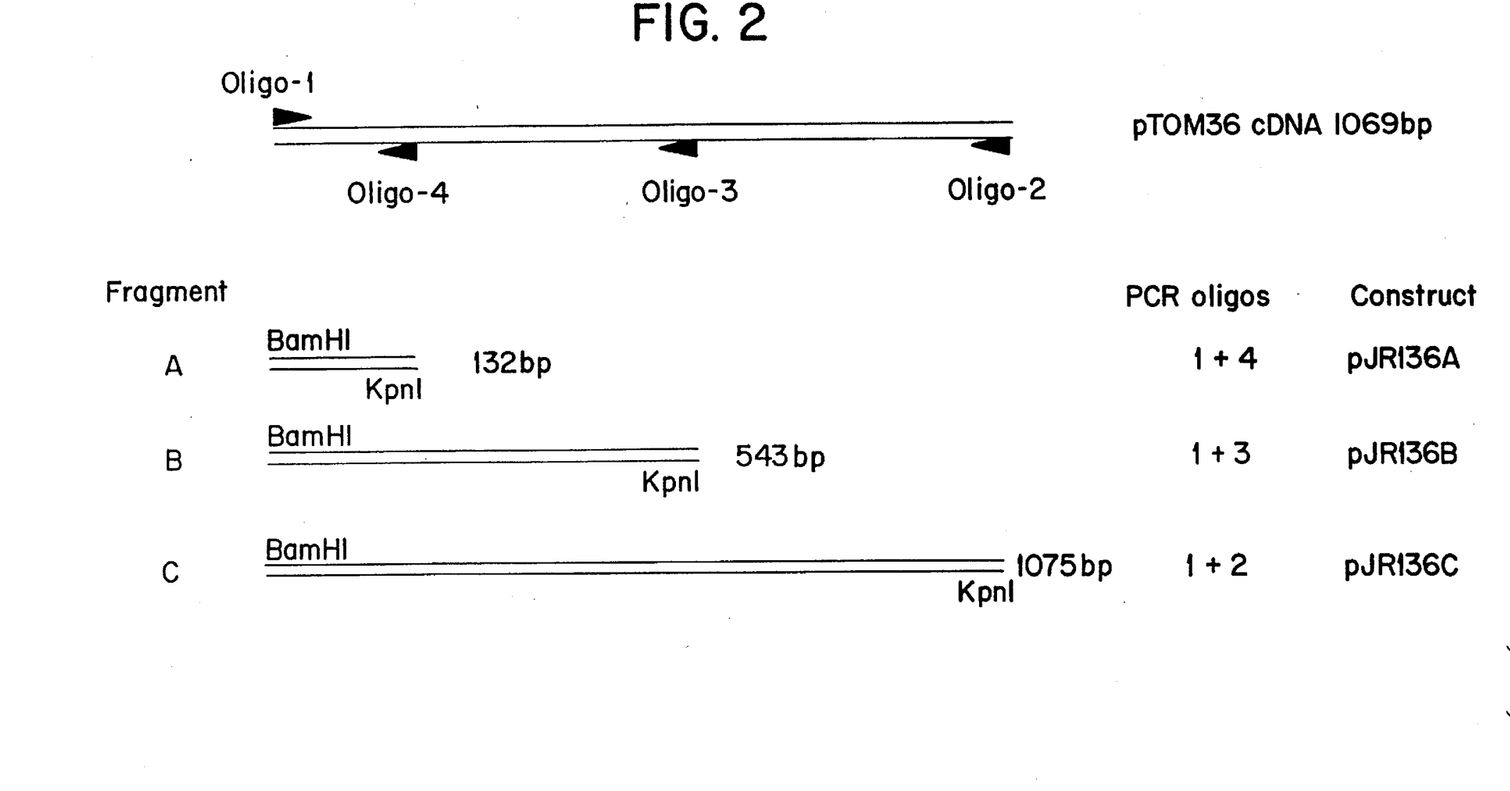
FIG. 2 show the regions of the pTOM36 sequence which may be synthesised by polymerase chain reaction (PCR) and used in the construction of antisense RNA vectors according to the invention.

A vector pJR136B was constructed using the sequence corresponding to Fragment B (bases 1–538) of the pTOM36 cDNA as shown in FIG. 2.

Figure 3:
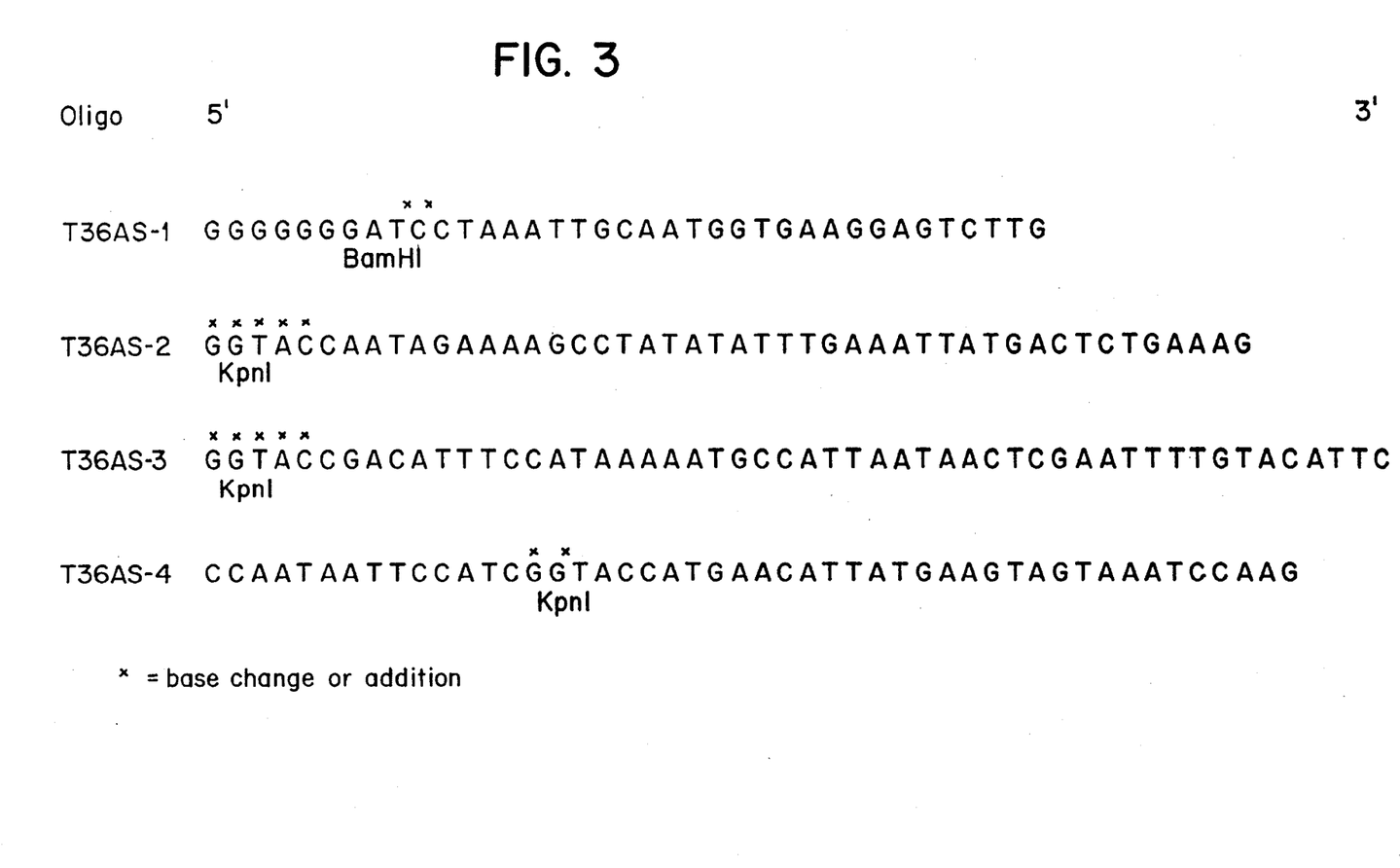
FIG. 3 show the base sequence of the oligonucleotides used as primers (SEQ ID No:2 to SEQ ID No:5) for the polymerase chain reactions to synthesise the fragments illustrated in FIG. 2.

This fragment was synthesised in vitro using polymerase chain reactions with the synthetic oligonucleotides 1 and 3 as shown in FIG. 2 as primers and pTOM36 cDNA as template. The synthetic oligonucleotide primers were designed such that a BamHI restriction site was incorporated at the 5' end of the fragment and a KpnI site was incorporated at the 3' end of the fragment: base sequences are shown in FIG. 3. After cleavage of the fragment with BamHI and KpnI, it was cloned into the vector pJR1 which had previously been cut with KpnI and BamHI, to give a vector which was named pJR136B. pJR1 (Smith et al Nature 334, 724–726, 1988) is a Bin19 ( Bevan, Nucleic Acids Research, 12, 8711–8721, 1984) based vector, which permits the expression of the antisense RNA under the control of the CaMV 35S promoter. This vector includes a nopaline synthase (nos) 3' end termination sequence.

After synthesis of the vector pJR136B, the structure and orientation of the pTOM36 sequence it contained were confirmed by DNA sequence analysis.

EXAMPLE 2B

Vectors pJR136A and pJR136C were prepared in the same way as pJR136B in Example 2A. They contain respectively bases 1 to 132 and bases 1 to 1069 (the complete cDNA) of pTOM36.

EXAMPLE 3A

Construction of pTOM36 antisense RNA vector with the polygalacturonase promoter.

The fragment produced in Example 2A by cleavage with BamHI and KpnI was also cloned into the vector pJR2 to give the clone pJR236B. pJR2 is a Bin19 based vector, which permits the expression of the antisense RNA under the control of the tomato polygalacturonase promoter. This vector includes a nopaline synthase (nos) 3' end termination sequence. This vector does not contain a KpnI or a BamHI site between the promoter and terminator sequences. Consequently, the PCR synthesised fragment was digested with KpnI and BamHI, the cut ends were made flush with T4 polymerase and then cloned into the HincII site of pJR2. After synthesis, the vector with the correct inverted orientation of pTOM36 sequence was identified by DNA sequence analysis.

EXAMPLE 3B

Clones similar to pJR236B were made from the fragments of Example 2B. These are:

1. Bases 1 to 132—pJR236A
2. Bases 1 to 1069—pJR236C

EXAMPLE 4

Construction of pTOM36 sense RNA vectors with the CaMV 35 promoter.

The fragments of pTOM36 cDNA described in Example 2 were also cloned into the vector pJR1 in the sense orientation to give the following clones:

1. Bases 1 to 132—pJR136AS
2. Bases 1 to 538—pJR136BS
3. Bases 1 to 1069—pJR136CS The PCR generated fragments were digested with KpnI and BamHI, the cut ends made flush with T4 polymerase and then cloned into the HincII site of pJR1. After synthesis, the vectors with the sense orientation of pTOM36 sequence were identified by DNA sequence analysis.

EXAMPLE 5

Experiments with pTOM36 antisense transformed tomatoes are described below.

Generation of transformed plants

Tomato plants were transformed with vector pJR136B (the pTOM36 antisense RNA vector described in Example 2 above).

Vectors were transferred to *Agrobacterium tumefaciens* LBA4404 (a micro-organism widely available to plant biotechnologists) and were used to transform tomato plants (*Lycopersicon esculentum*, vat. Ailsa Craig). Transformation of tomato stem segments followed standard protocols (e.g. Bird et al Plant Molecular Biology 11, 651–662, 1988. Thirty-six plants were selected as transformed by their ability to produce roots on media containing kanamycin. These plants were grown to maturity in the glasshouse.

Analysis of transformed plants

Visual appearance.

The majority of plants grew normally and produced fruit which appeared to ripen normally. Previous experience with populations of primary transformants indicates that a few plants have abnormal growth habit and/or do not set fruit. This was also observed with the pTOM36 antisense plants. pTOM36 related mRNA levels in the fruit.

In order to determine whether the transformed plants had reduced expression of pTOM36 related genes, total RNA was extracted from ripe fruit from 11 plants. RNA (Northern) blots of this extracted RNA were probed with radiolabelled probe for the pTOM36 sense strand. This probe hybridises to RNA molecules of three sizes (1.45, 2.0, 2.8 kb) from unmodified tomato fruit. These RNA species were detected in RNA extracted from all of the modified plants. However, major reductions in the abundance of all 3 RNA species was observed in RNA from five of the modified plants.

Selection of plants with single sites of insertion of the antisense gene.

In order to select plants with single sites of insertion that would give simple segregation patterns in future generations, genomic DNA was extracted from leaves of the plants with reduced levels of pTOM36 related RNA in the fruit. DNA (Southern) blots were prepared with this genomic DNA after digestion with HindIII. The blots were probed with radiolabelled insert from the pTOM36 cDNA. This probe hybridised to a DNA fragment of 4.4 kb from unmodified plants. Additional hybridising fragments in the digested DNA from the modified plants were interpreted to represent individual sites of insertion of the pTOM36 antisense gene. One plant, E56C37, was identified as having a single site of insertion and was selected for analysis of progeny.

Analysis of dry weights and sugar content of fruit from primary transformants.

The dry weights and reducing sugar content of pericarps from ripe fruit were analysed. Fruit from some individual plants from the population of primary transformants had significantly greater dry weight/fresh weight ratio and sugar content than unmodified fruit. Fruit from E56C37 and a second transformant, E56C1, had approximately 5 and 9% increases in dry weight/fresh weight ratio respectively.

Analysis of progeny

Identification of homozygous and azygous selfed progeny.

Plants homozygous or azygous (null) for the pTOM36 antisense gene were identified in populations of self-fertilised progeny from E56C37. In addition, the pTOM36 antisense gene segregated as a single site of insertion in selfed progeny of E56C1. These plants were chosen as the parents of modified or unmodified lines for extensive analysis:

| Parent | Line | Genotype |
|--------|------|----------|
| E56C37 | L1AC36A | Homozygous |
|        | L2AC36A | Azygous |
| E56C1  | L3AC36A | Homozygous |
|        | L4AC36A | Azygous |

1991 Glasshouse trials of modified lines.

In late Summer 1991 lines L1AC36A (homozygous), L2AC36A (azygous) and unmodified Ailsa Craig were grown in large scale glasshouse trials in the UK.

Plants were grown in a fully replicated block trial. Fruit were harvested at 5 ripening stages (3, 5, 7, 10 and 14 days post breaker—'dpb') and analysed for colour, firmness, survivability, dry weight/fresh weight ratio and sugar content. The experiment was replicated 3 times during the season. Analysis of variance was used to identify significant differences between the lines.

Survivability and firmness of the homozygous fruit were not significantly different from the azygous and unmodified fruit. The colour index was slightly enhanced compared to both control lines.

Over the 5 ripening stages the mean dry weight as a percentage of fresh weight of L1AC36A fruit was significantly ($p<0.001$) enhanced (by more than 5%) compared to both the azygous and the unmodified control lines. The greatest increase was observed in later stages of ripening (13.5% increase at 14 dpb).

The reducing sugar, acids (malic and citric) and aqueous alcohol insoluble solids contents of the dried pericarp samples were determined. There were no significant differences in the acids and aqueous alcohol insoluble solids contents between the homozygous fruit and fruit from the two control lines.

The sugars (which comprise 50% of the solids content of tomato) were significantly greater in the homozygous than in the azygous fruit. This increase in sugars content was sufficient to account for the greater solids content of the homozygous fruit.

However, there was no significant difference between the sugars content of the homozygous and the unmodified Ailsa Craig fruit, despite the greater dry weight content of the homozygous fruit. Thus the compositions of the two control fruit were apparently different.

These experiments confirm that the increased percentage dry weight is associated with the presence of the pTOM36 antisense fruit. In addition, the difference in sugar contents of the homozygous and azygous lines indicates that increased sugars has segregated with the presence of the pTOM36 antisense gene. The reason for the differences between the sugar contents of the two control lines is not yet clear.

Further trials with Lines L1AC36A, L2AC36A, L3AC36A and L4AC36A were carried out in 1992. These trials did not however show significant increases in solids content for homozygous as compared with azygous lines. The reason for this is not clear, but may be attributable to environmental factors such as altered growing conditions.

We claim:

1. A method of producing fruit having increased solids content which comprises transforming fruit-bearing plants with a DNA construct adapted to inhibit expression of the pTOM36 gene during ripening, selecting transgenic plants in which expression of the pTOM36 gene is at least partially inhibited when compared to expression in non-transformed plants, cultivating said transgenic plants or progeny thereof and harvesting the fruit which shows an increase in dry weight to fresh weight ratio of about 5–14%, wherein the DNA construct comprises a DNA sequence encoded by the clone pTOM36 under control of a promoter functional in plants so that the DNA sequence generates RNA during ripening, said RNA being sense or antisense RNA and wherein the fruit is tomato.

2. Tomatoes produced by the method of claim 1.

* * * * *